(12) United States Patent
Brecher

(10) Patent No.: US 7,054,754 B1
(45) Date of Patent: May 30, 2006

(54) METHOD, SYSTEM, AND SOFTWARE FOR DERIVING CHEMICAL STRUCTURAL INFORMATION

(75) Inventor: Jonathan S. Brecher, Cambridge, MA (US)

(73) Assignee: Cambridgesoft Corporation, Cambridge, MA (US)

( * ) Notice: Subject to any disclaimer, the term of this patent is extended or adjusted under 35 U.S.C. 154(b) by 0 days.

(21) Appl. No.: 09/502,810

(22) Filed: Feb. 11, 2000

Related U.S. Application Data

(60) Provisional application No. 60/119,930, filed on Feb. 12, 1999.

(51) Int. Cl.
 G06F 19/00 (2006.01)
 G06F 17/00 (2006.01)
 G06F 17/20 (2006.01)
(52) U.S. Cl. .............................. 702/19; 704/1
(58) Field of Classification Search ............ 702/19, 702/22, 27; 395/500.23; 704/1–10
See application file for complete search history.

(56) References Cited

U.S. PATENT DOCUMENTS

| 4,473,890 A | * | 9/1984 | Araki |
| 5,345,516 A | * | 9/1994 | Boyer et al. ............... 382/10 |
| 5,874,564 A | * | 2/1999 | Ecker et al. ............... 536/24.5 |

OTHER PUBLICATIONS

Ihlenfeldt et al., Journal of Chemical Information and Computer Sciences, vol. 35, No. 4, Jul. -Aug., 1995 (Abstract only).*
Chem Draw; Chemical Structure Drawing Standard [Publ. Cambridge-Soft. Corp., 100 Cambridge Park Dr., Cambridge, MA 02140] pp. 69-69, 1997.*
New Riverside University Dictionary, Riverside Publishing Company, Boston, MA 02108-1984 p. 783, 1984.*
Ruiz, et al., "Error Detection, Recovery, and Repair in the Translation of Inorganic Nomenclatures. 1.A Study of the Problem", *J. Chem. Inf. Comput. Sci.*, vol. 36(1), pp. 7-15, (1996).
Cooke-Fox, et al., "From names to diagrams—by computer", *Chemistry in Britain*, pp. 467-471 (1985).
Cooke-Fox, et al., "Computer Translation of IUPAC Systematic Organic Chemical Nomenclature. 1. Introduction and Background to a Grammar-Based Approach", *J. Chem. Inf. Comput. Sci.*, vol. 29, pp. 101-105 (1989).
Brecher, "The ChemFinder WebServer: Indexing Chemical Data on the Internet", *CHIMIA*, vol. 52, pp. 658-663 (1998).
Vander Stouw, et al., "Procedures for Converting Systematic Names of Organic Compounds into Atom-Bond Connection Tables", *Journal of Chemical Documentation*, vol. 7(3), pp. 165-169 (1967).

Vander Stouw, et al., "Automted Conversion of Chemical Substances Names to Atom-Bond Connection Tables", *Journal of Chemical Documentation*, vol. 14(4), pp. 185-193 (1974).
Stillwell, "Computer Translation of Systematic Chemical Nomenclature to Structural Formulas-Steroids", *Journal of Chemical Documentation*, vol. 13(3), pp. 107-109 (1973).
Ihlenfeldt, et al., "Augmenting Connectivity Information by Compound Name Parsing: Automatic Assignment of Stereochemistry and Isotape Labeling", *J. Chem. Inf. Comput. Sci.*, vol. 35, pp. 663-674.
Cooke-Fox, et al., "Computer Translation of IUPAC Systematic Organic Chemical Nomenclature. 2. Development of a Formal Grammar", *J. Chem. Inf. Comput. Sci.*, vol. 29, pp. 106-112 (1989).
Cooke-Fox, et al., "Computer Translation of IUPAC Systematic Organic Chemical Nomenclature. 3. Syntax Analysis and Semantic Processing", *J. Chem. Inf. Comput. Sci.*, vol. 29, pp. 112-118 (1989).
Cooke-Fox, et al., "Computer Translation of IUPAC Systematic Organic Chemical Nomenclature. 4. Concise Connection Tables to Structure Diagrams", *J. Chem. Inf. Comput. Sci.*, vol. 30, pp. 122-127 (1990).
Cooke-Fox, et al., "Computer Translation of IUPAC Systematic Organic Chemical Nomenclature. 5. Steroid Nomenclature", *J. Chem. Inf. Comput. Sci.*, vol. 30, pp. 128-132 (1990).
Kirby, et al., "Computer Translation of IUPAC Systematic Organic Chemical Nomenclature. 6. (Semi) automatic Name Correction", *J. Chem. Inf. Comput. Sci.*, vol. 31, pp. 153-160 (1991).
Helson, "Structure Diagram Generation", *Reviews in Computational Chemistry*, Lipkowitz, K.B., Boyd, D.B., Eds.; Wiley-VCH: New York, vol. 13 Chapter 6, pp. 313-398 (1999).
ChemInovation Software, "Chemistry 4-D Draw User's Guide", pp. 1-61 (1997).
Cambridge Scientific Computing Inc., "Chem3D The Molecular Modeling System", pp. 1-337 (1990).

* cited by examiner

*Primary Examiner*—Marianne P. Allen
(74) *Attorney, Agent, or Firm*—Wilmer Cutler Pickering Hale and Dorr

(57) ABSTRACT

A method and a system are provided for deriving chemical structures from chemical names. Chemical name fragments are grouped into a number of classifications. The method and the system handle new and old chemical names, including names for organic and inorganic substances. The method and the system handle inverted names, including inverted names with missing commas or with extraneous spaces.

18 Claims, 14 Drawing Sheets

Microfiche Appendix Included
(4 Microfiche, 382 Pages)

Table 1: Strings that cannot terminate fragments to be prepended

| "dry" | "ed" | "ide" | "ing" | "mm" | "one" | "rod" |
|---|---|---|---|---|---|---|

FIG. 5A

Table 2: Strings that cannot initiate fragments to be prepended (note that some strings include a space character)

| |
|---|
| "in " |
| "ion" |
| "low " |

FIG. 5B

Table 3: Strings that cannot appear anywhere in fragments to be prepended (note that some strings include one or more space characters)

| | | |
|---|---|---|
| " and " | "grade" | "radical" |
| " in " | "granul" | "random" |
| " ion" | "grease" | "reagent" |
| "%" | "grit" | "reduc" |
| "/" | "hbr" | "regular" |
| "7ci" | "hcl" | "remainder" |
| "8ci" | "heavy" | "ribbon" |
| "9ci" | "hydrin" | "rods" |
| "10ci" | "hydrous" | "salt" |
| "aas" | "ide " | "scale" |
| "absolute" | "imine" | "shot" |
| "acid" | "ing" | "slug" |
| "acs" | "inhibit" | "soluble" |
| "aerosol" | "isotop" | "solution" |
| "amidine" | "ite" | "sphere" |
| "analy" | "ize" | "spong" |
| "approx" | "lactam" | "stab" |
| "assay" | "lacton" | "stabil" |
| "ate" | "light" | "standard" |
| "balance" | "lump" | "stick" |
| "basic" | "mainly" | "sublim" |
| "basis" | "medium" | "sultam" |
| "bead" | "mesh" | "sulton" |
| "briquette" | "micron" | "synthetic" |
| "catal" | "ml" | "syrup" |
| "certif" | "mm " | "tablet" |
| "chip" | "moist" | "tech" |
| "chunk" | "morphous" | "tion" |
| "cm" | "mossy" | "titrant" |
| "coarse" | "natural" | "tone" |
| "contain" | "needle" | "typic" |
| "crucible" | "neutral" | "usp" |
| "cryst" | "nitrile" | "wire" |
| "deriv" | "pearl" | "with" |
| "dispers" | "pellet" | "xime" |
| "dry " | "piece" | "zone" |
| "dust" | "plate" | |
| "ed " | "poly" | |
| "electro" | "porous" | |
| "ester" | "powder" | |
| "ether" | "ppm" | |
| "fcc" | "pract" | |
| "fine" | "predomina" | |
| "flake" | "predominantly" | |
| "foil" | "protected" | |
| "for " | "puratronic" | |
| "from" | "pure" | |
| "glacial" | "purity" | |
| | "purum" | |

FIG. 5C

Table 4.

ether
sulfide
disulfide
trisulfide
tetrasulfide
pentasulfide
hexasulfide
selenide
diselenide
triselenide
telluride
sulfone
disulfone
trisulfone
sulfoxide
disulfoxide
trisulfoxide
peroxide
ketone
diketone
triketone
tetraketone

FIG. 5D

| CONNECTION TABLE | | | | |
|---|---|---|---|---|
| |  | 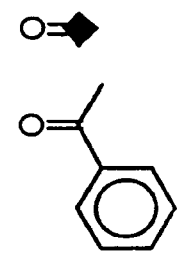 |  | |
| NAME | naphth | oxy | phenac | yl | bromide |
| TYPE | unknown | opfuser | infix | root | enderaminoacid | counterion |
| SUBTYPE | unknown | unknown | doublebondable | root | yl | ionable |
| PREV CHAR | '(' | 'a' | 'a' | 'a' | '' |

FIG. 7A

| CONNECTION TABLE | | | | |
|---|---|---|---|---|
| |  | 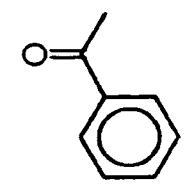 |  | |
| NAME | p | naphth | oxy | phenac | yl | bromide |
| TYPE | unknown | opfuser | infix | root | suffix | counterion |
| SUBTYPE | unknown | unknown | doublebondable | root | yl | ionable |
| PREV CHAR | '(' | 'a' | 'a' | 'a' | '' |

FIG. 7B

| CONNECTION TABLE |  |  | | |
|---|---|---|---|---|
| NAME | naphth | oxy | phenac | bromide |
| TYPE | root | infix | root | counterion |
| SUBTYPE | unknown | doublebondable | root | ionable |
| PREV CHAR | '(' | 'a' | 'a' | |

| | | | | |
|---|---|---|---|---|
| | unknown | | yl | |
| | unknown | | suffix | |
| p | | | yl | |
| unknown | | | 'a' | |

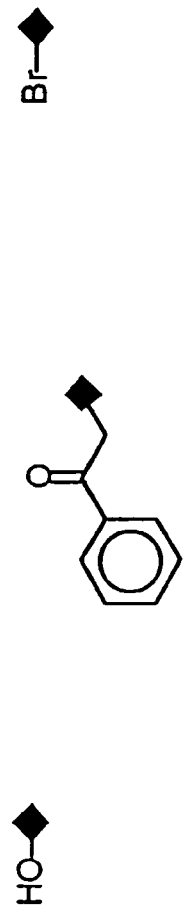
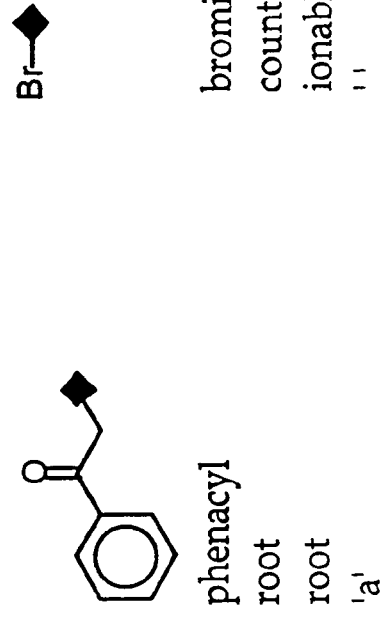
FIG. 7D
FIG. 7E

METHOD, SYSTEM, AND SOFTWARE FOR DERIVING CHEMICAL STRUCTURAL INFORMATION

CROSS-REFERENCE TO RELATED APPLICATIONS

This application claims the benefit of U.S. Provisional Application Ser. No. 60/119,930 entitled DERIVING A CHEMICAL STRUCTURE FROM A CHEMICAL NAME filed on Feb. 12, 1999, incorporated herein.

REFERENCE TO MICROFICHE APPENDIX

A microfiche appendix forms part of this application. The appendix, which includes a source code listing relating to an embodiment of the invention, includes 382 frames on 4 sheets of microfiche.

This patent document (including the source code appendix) contains material that is subject to copyright protection. The copyright owner has no objection to the facsimile reproduction by anyone of the patent document as it appears in the Patent and Trademark Office file or records, but otherwise reserves all copyright rights whatsoever.

BACKGROUND OF THE INVENTION

This application relates to deriving chemical structural information.

A chemical substance is commonly represented in textual form ("name") or graphical form ("structure"), each of which has its own advantages. For example, a name such as "benzene" is well-suited for use in a conversational or written statement such as "The object was immersed in 100% benzene." Benzene can also be represented by a structure (FIG. 1) that illustrates that a benzene molecule features high symmetry, including six carbon atoms arranged at the corners of a regular hexagon, with six hydrogen atoms arranged a fixed distance outward from respective corners.

A chemical substance can have multiple chemical names. For example, benzene is also known as "benzol", "cyclohexatriene", "1,2,3-cyclohexatriene", "cyclohexa-1,2,3-triene", "[6]annulene", and "1-carbapyridine". Some names are sanctioned by at least one of three major organizations that have developed chemical nomenclature systems: the International Union of Pure and Applied Chemistry ("IUPAC"), the International Union of Biochemistry and Molecular Biology ("IUBMB"), and the Chemical Abstracts Service ("CAS"), a division of the American Chemical Society ("ACS"). These organizations often disagree about the preferred name for a substance, and the recommendations from each organization tend to be complex and have changed over time. In many instances, chemists produce or use chemically correct names that vary from the "sanctioned" names. Unintentional errors such as typographical errors are common.

Chemical names are commonly found in one of two general forms, known as "normal" (e.g., "O-acetylsalicylic acid") and "inverted" (e.g., "salicylic acid, O-acetyl-"). Each form has its utility. The normal form corresponds to regular English writing style, is read from left to right, and is appropriate for use in prose. The inverted form emphasizes the main chemical feature of the substance and is particularly well suited for indexing, since the inverted form allows substances of similar chemistry to be sorted together, alphabetically. Many chemical names are available only in inverted form.

The abundance of different names for the same chemical substance can create confusion and uncertainty when one chemist attempts to understand a written document produced by another chemist. Chemical structures, on the other hand, tend to cause less confusion and uncertainty.

SUMMARY OF THE INVENTION

A method and a system are provided for deriving, from chemical names, corresponding structures with high accuracy and comprehensiveness. An implementation in a high speed computer allows chemical names to be accurately converted to chemical structures in real time or nearly in real time, which provides users with a powerful, practical tool for use in situations where structural representations offer substantial advantages. In at least some cases, the method and the system are able to derive such structures where the names do not conform to any sanctioned nomenclature system. By grouping chemical name fragments into a small number of classifications, the method and the system feature flexibility that facilitates application of the method and the system to new chemical names as well as old chemical names, including names for organic and inorganic substances. The method and the system handle inverted names, including inverted names with missing commas or with extraneous spaces.

Other features and advantages will become apparent from the following description, including the drawings, and from the claims.

BRIEF DESCRIPTION OF THE DRAWINGS

FIGS. 5A–5D, and 6 are illustrations of computer data.
FIGS. 7A–7G are illustrations of output produced by software.

DETAILED DESCRIPTION

This application is filed simultaneously with a United States patent application entitled ENHANCING STRUCTURE DIAGRAM GENERATION, Ser. No. 09/502,133, which is incorporated herein.

Figure 1:
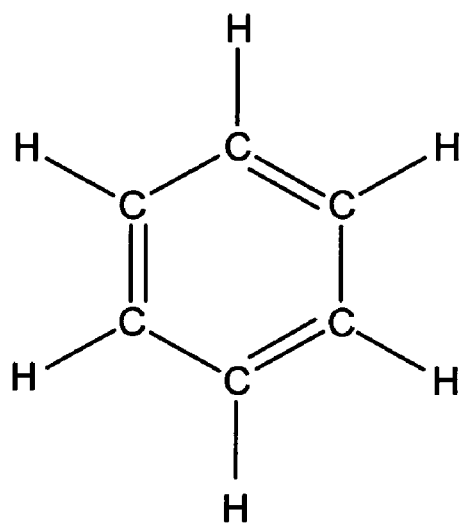
FIG. 1 is an illustration of a chemical structure.
Figure 2:
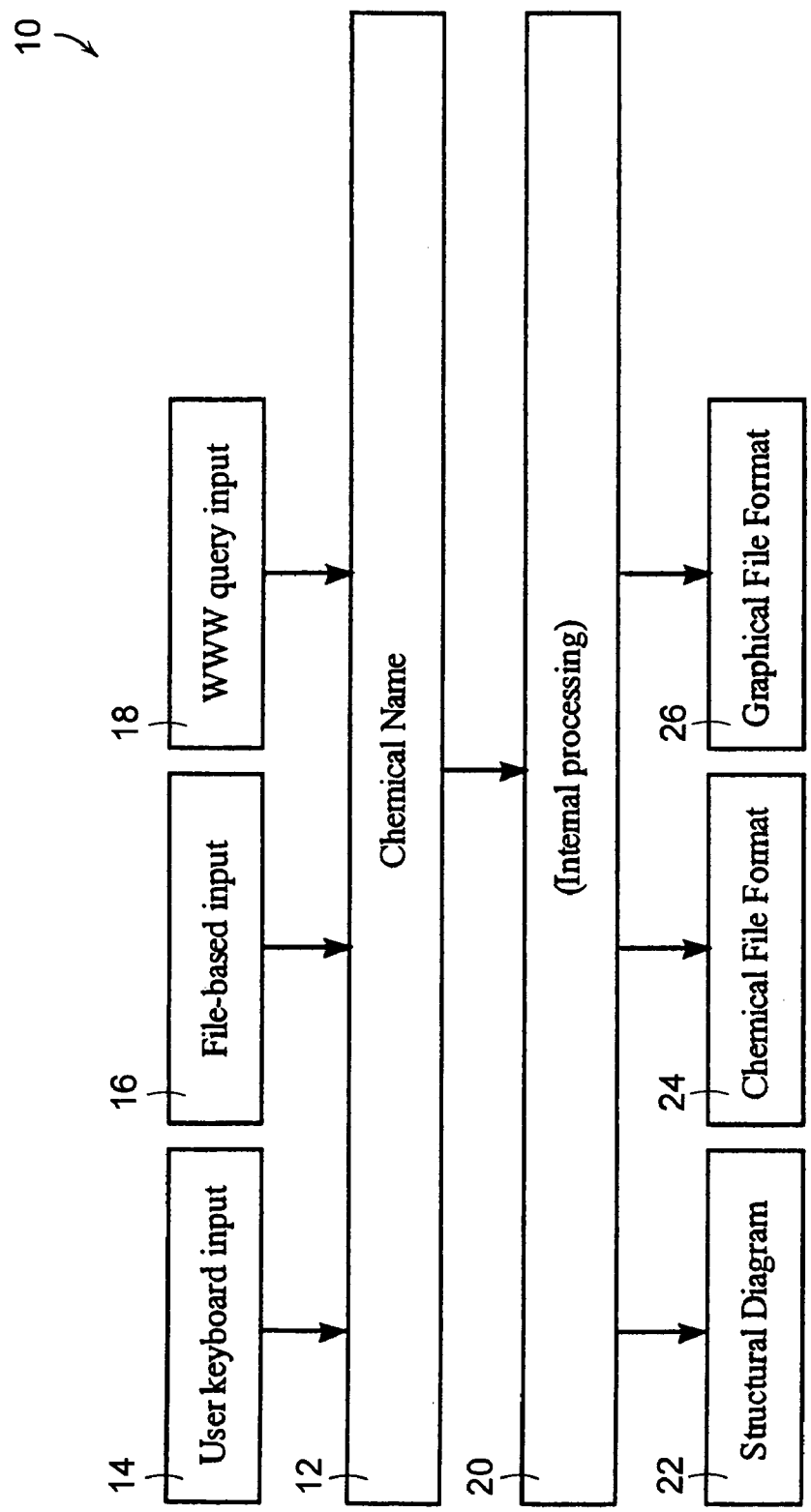
FIG. 2 is a block diagram of computer-based systems.

FIG. 2 illustrates a structure derivation system 10. A chemical name 12 is supplied via one or more input systems such as end-user keyboard input 14, file-based input 16, or World-Wide Web query input 18. The chemical name is received by computer-based internal processing 20, which derives structural output in one or more forms such as a diagram 22 displayed on paper or on a screen, a chemical format file 24, or a graphical format file 26. One or more of the output forms may be derived from another of the output forms, e.g., by scanning a paper printout into a computer file, or by using a graphic display program to display or print a diagram based on the contents of a format file.

In general, in a preferred embodiment, the internal processing operates by comparing portions of the chemical name to text strings that have been predetermined to have respective characteristics and properties in accordance with rules of chemical nomenclature, and with exceptions to such rules, and assembling a structure from pieces corresponding to selected text strings, as described below.

Figure 3A:
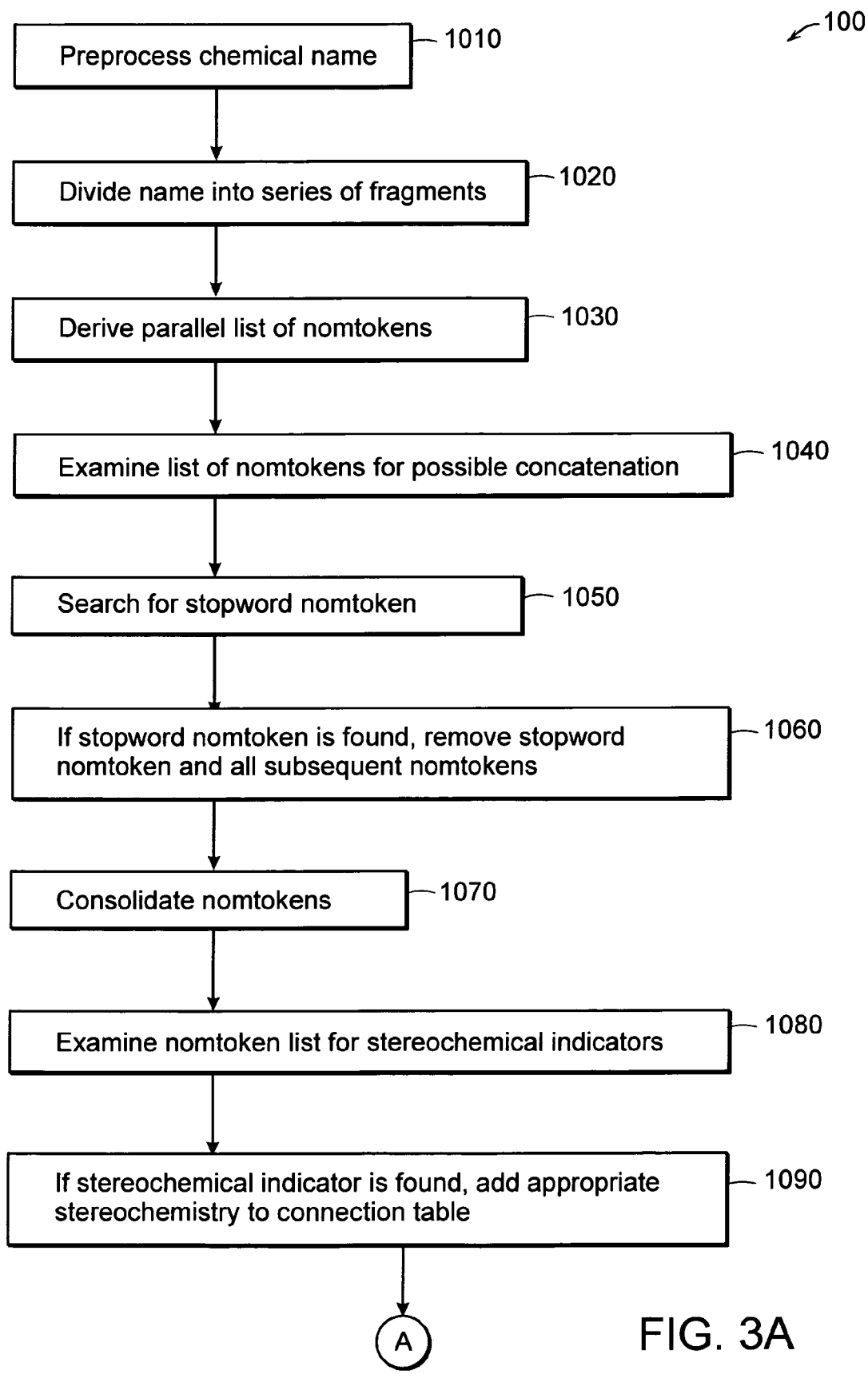
FIGS. 3A–3B and 4 are flow diagrams of computer-based procedures.
Figure 3B:
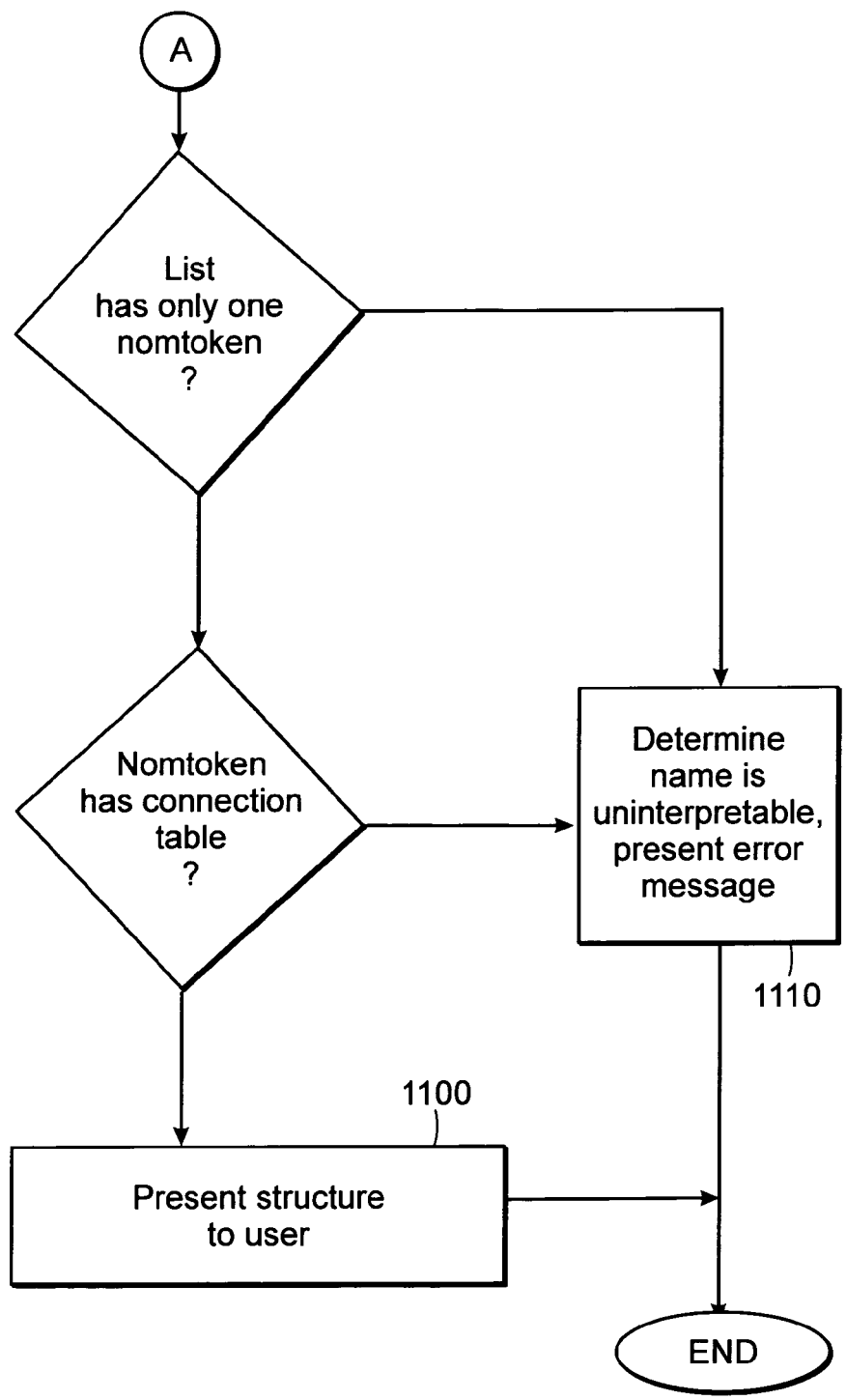

FIGS. 3A–3B illustrate a method 100 of the internal processing, which is applied in a specific example ("Phenacyl bromide, p-napthoxy") after the following description. The chemical name ("original input name") is preprocessed to standardize its formatting and to simplify subsequent operations (step 1010). In an initial stage of the preprocessing, the individual characters of the name are manipulated as follows without reference to the chemical meaning implied by the characters. The name is converted to all lower-case characters. Common typographical errors, including errors that relate to inadvertent addition, deletion, or transposition of characters, are identified using substring searches and are corrected. Uncommon characters of chemical significance are spelled out using common characters, so that, for example, the character "μ" ("μ") is changed to "mu".

Figure 4:
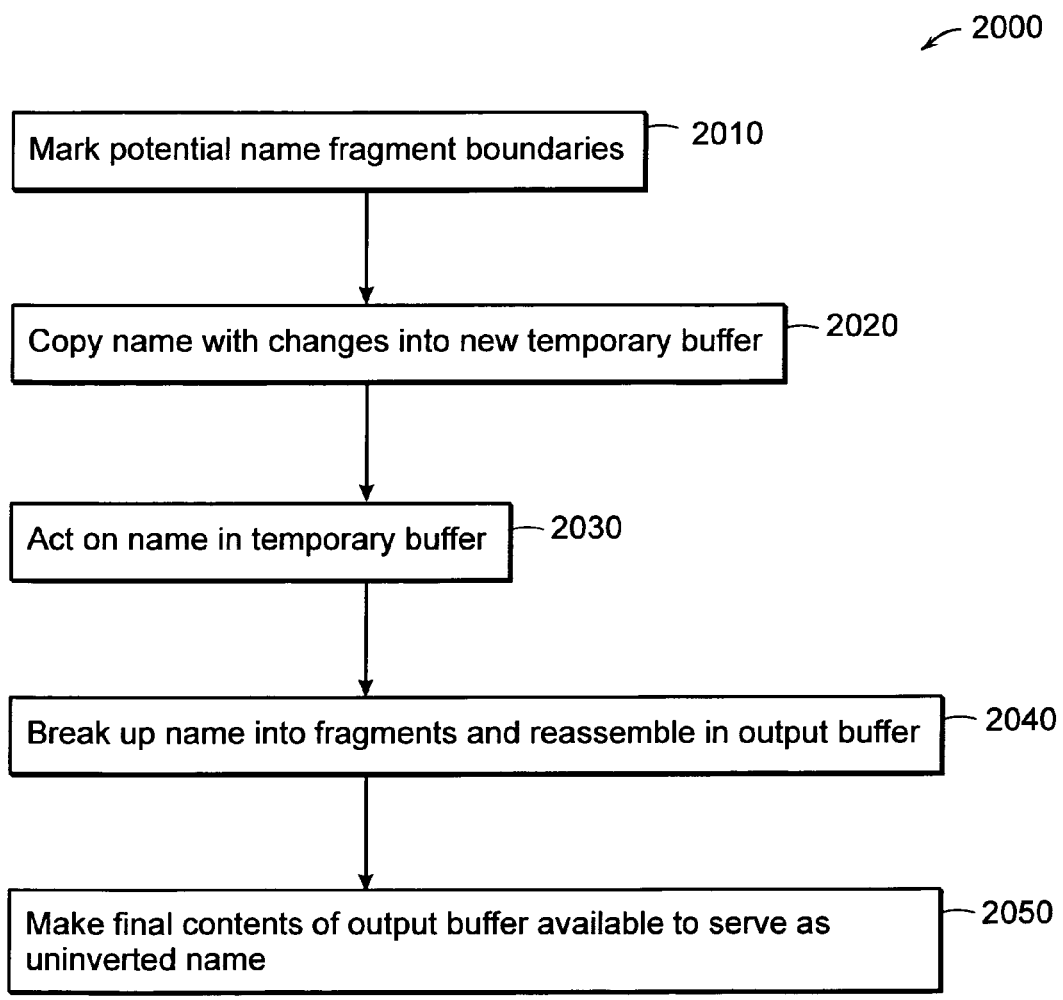

Also during the preprocessing, if the name or a portion of the name has been submitted in inverted form (e.g., "acetic acid, 2-hydroxy-"), the name or portion is converted to its uninverted form (e.g., "2-hydroxyacetic acid") by a procedure 2000 (FIG. 4). A chemical name is uninverted by identifying name fragment boundaries and reordering the name fragments in accordance with a normal form. Commas are common delimiters of such name fragments, but other delimiters are found as well, and not all commas serve as boundaries. In the identification, false boundaries are determined from context and are discarded.

In the uninversion process, fragments are reordered after all fragments are identified, and context is observed. An inverted name of the form a/b/c/d/e may or may not uninvert to e/d/c/b/a; the name may become e/b/a/c/d or any of several other possibilities. The contents of each fragment are examined to determine the fragment's proper position relative to preceding fragments.

The uninversion process includes the following steps (FIG. 4). The input name is analyzed to mark all potential name fragment boundaries (step 2010). In a specific embodiment, the mark used is an @ sign, which is rarely used in chemical names. In another embodiment, it may be advantageous to use a non-printing character such as control-A (ASCII value 1) that has effectively no chemical significance.

The name is scanned from left to right and is copied, possibly with changes as now described, into a new temporary buffer (step 2020). During scanning, open- and close-parentheses and other enclosing marks are counted, and depths of enclosing marks are monitored. With some exceptions, characters are copied to the new buffer unmodified. Commas that are not enclosed within any level of enclosing marks are not copied, but are instead converted to @ signs. For simplicity, any space characters or additional commas immediately following such a comma are treated as having no syntactic significance, and are not copied.

Hyphens are also examined during the scan. If a hyphen is immediately followed by a space character and is not immediately preceded by a comma or a plus ("+") or slash ("/") character, the hyphen is converted to an @ sign. Any space characters or additional commas immediately following such a hyphen are treated as having no syntactic significance, and are ignored. Such treatment addresses a common typographical error of omitting a comma, such as the comma that should be present before the final word in "benzoic acid, 2-chloro-oxime".

An apostrophe that immediately precedes a digit is also assumed to represent the typographical omission of a comma, and is treated as if a comma were present. Thus, a comma is inserted between the two pertinent characters, unless the characters are not enclosed in any levels of enclosing marks such as parentheses, in which case an @ sign is inserted instead.

From this point, actions occur within the temporary buffer (step 2030) and do not to change the length of the buffer, which has the same length as the name in the buffer.

The buffer is scanned for the presence of a text string ("substring") "+@–", which, if found, is replaced by a substring "+,–".

The buffer is scanned for the presence of a substring "mer" followed by any character except "c". Since such a sequence, if present, indicates with high likelihood the presence of a polymer descriptor such as a monomer, dimer, or oligomer descriptor in the remainder of the string, any @ signs present in the remainder of the string, i.e., to the right of the "mer" substring, are converted to spaces. Determining whether the "mer" substring is followed by the character "c" is important to avoid misinterpreting mercury compounds as polymers, so that, for example, "acetic acid@mercury (ii) @hydrate" is not erroneously converted to "acetic acid@mercury (ii) hydrate".

The buffer is scanned for any single one of the characters "0", "1", "2", "3", "4", "5", "6", "7", "8", "9", "?", or an apostrophe, that is immediately followed by any number (i.e., including zero) of the characters "]", ")", "}", or "h", in any order, but that is not preceded by the character "d". If such a sequence is found, any @ sign that immediately follows the sequence is converted to a comma, so that, for example, "1h@3h@5h@2@4@6-pyrimidinetrione" is properly converted to "1h,3h,5h,2,4,6-pyrimidinetrione".

If the final character of the buffer is a hyphen, and the last @ sign, if present, in the buffer is preceded immediately by a single one of the characters "]", ")", or "}", which is in turn preceded by any single one of the characters "0", "1", "2", "3", "4", "5", "6", "7", "8", "9", "?", or an apostrophe, the last @ sign is converted to a comma.

The buffer is scanned for any single one of the characters "0", "1", "2", "3", "4", "5", "6", "7", "8", "9", "?", or an apostrophe, followed immediately by a close parenthesis, followed immediately by any number of the characters "]", ")", or "}", followed immediately by an @ sign, followed immediately by any single one of the characters "0", "1", "2", "3", "4", "5", "6", "7", "8", "9", or "?". If such a sequence is found, the @ sign is converted to a comma.

The buffer is scanned for an @ sign immediately preceding any single one of the characters "0", "1", "2", "3", "4", "5", "6", "7", "8", "9", "?", "a", "b", "A", or "B". If such an @ sign is found where that preceding character is preceded by either of the characters "a" or "b", which is preceded by any of the characters "(", "0", "1", "2", "3", "4", "5", "6", "7", "8", "9", "?" or a comma or an apostrophe, the @ sign is converted to a comma. Accordingly, for example, "4aa@8ab-dihydronaphthalene" is properly converted to "4aa,8ab-dihydronaphthalene".

The buffer is scanned for an @ sign immediately preceding any single one of the characters "0", "1", "2", "3", "4", "5", "6", "7", "8", "9", "?", or an apostrophe, where character precedes any single one of the characters ")", "]", "}", "e", "z", "r", "s", "E", "Z", "R", or "S". If such an @ sign is found that is preceded by any single one of the characters "e", "z", "E", or "Z", which is preceded by any of the characters "(", "[", "{", "0", "1", "2", "3", "4", "5", "6", "7", "8", "9", "?" or a comma or an apostrophe, the @ sign is converted to a comma.

The buffer is scanned for an @ sign immediately preceding any single one of the characters "0", "1", "2", "3", "4", "5", "6", "7", "8", "9", "?", "a", "b", "A", "B", or an apostrophe, where such character itself precedes any single one of the characters "e", "z", "r", "s", "E", "R", or "S", or a period. If such an @ sign is found that is preceded by any number of the characters ")", "]", "}", or "*", which is preceded by any one of the characters "r", "s", "R", or "S", which is preceded by any of the characters "(", "[", "{", "0", "1", "2", "3", "4", "5", "6", "7", "8", "9", "a", "b", "A", "B", "?" or a comma or an apostrophe, the @ sign is converted to a comma.

The buffer is scanned for any occurrences of the strings "@ar@" or ",ar@". Any such string that is found is converted to ",ar,".

The buffer is scanned for an @ sign immediately preceding any number of periods, where such periods (if any) themselves precede either i) any single one of the characters "0", "1", "2", "3", "4", "5", "6", "7", "8", "9", "?", "n", "o", "p", "s", "N", "O", "P", or "S"; or ii) any of the text strings "cis", "trans", "alpha", "beta", "gamma", "delta", or "epsilon". If such an @ sign is found that is preceded by any number of apostrophes or periods, which are preceded by any one of the strings "alpha", "beta", "gamma", "delta", "cis", or "trans", the @ sign is converted to a comma.

The buffer is scanned for an @ sign immediately preceding any number of periods, where such periods (if any) precede either i) any single one of the characters "0", "1", "2", "3", "4", "5", "6", "7", "8", "9", "?", "n", "o", "p", "s", "N", "O", "P", or "S"; or ii) any of the text strings "ortho", "meta", or "para". If such an @ sign is found that is preceded by any number of apostrophes or periods, which are preceded by any one of the strings "ortho", "meta", or "para", the @ sign is converted to a comma.

The buffer is scanned for an @ sign immediately preceding any number of periods, where such periods (if any) precede either i) any single one of the characters "0", "1", "2", "3", "4", "5", "6", "7", "8", "9", "?", "n", "o", "p", "s", "N", "O", "P", or "S"; or ii) any of the text strings "cis", "trans", "alpha", "beta", "gamma", "delta", or "epsilon". If such an @ sign is found that is preceded by any number of the characters "0", "1", "2", "3", "4", "5", "6", "7", "8", "9", or an apostrophe, which are preceded by any single one of the characters "n", "o", "p", "s", "N", "O", "P", or "S", which is preceded by either i) no characters at all or ii) any single one of the characters "(", "[", "{", "-", an apostrophe, a comma, or a space, the @ sign is converted to a comma.

The foregoing regarding buffer scanning is also described by the following text strings formatted in accordance with regular expression notation, as described in Friedl, Jeffrey E. and Oram, Andy, eds., *Mastering Regular Expressions*, O'Reilly & Associates, 1997.

s/+@-/+,-/gi s/(@.*mer[^c].*)@/$1,/gi s/([^d][0-9\?\ ][ ]\h]*)@/$1,/gi s/([0-9\?\ ]\))@([^@]*-$)/$1,$2/gi s/([0-9\ \?]\)[ ]\)]*)@([0-9\?])/$1,$2/gi s/([\(, 0-9\ \?][ab])@([0-9\?ab])/$1,$2/gi s/([0-9, \(\[ ][ez])@([0-9\ \?]*[ ]ezrs\)])/$1,$2/gi s/([0-9ab, \(\[ ][rs][ ]\*\)]*)@([0-9ab\ \?]*[rsez\.])/$1,$2/gi s/([@,]ar@)\,ar,\gi s/(alpha|beta|gamma|delta|cis|trans)[\. ]*\.*([nops0-9\?] |cis|trans|alpha|beta|gamma|delta Ita|epsilon)/$1,$2/gi s/(ortho|meta|para)[\. ]*\.*([nops0-9\?]|ortho|meta|para)/ $1,$2/gi s/([[@, \-\({][nops][0-9\ ]*\.*([nops0-9\?] |alpha|beta|gamma|delta|epsilon)/$1,$2/gi All remaining @ signs are treated as true name fragment boundaries, so that the buffer is broken into fragments at the @ signs and is reassembled as follows (step 2040) in an output buffer created to store a final string.

The first fragment is added to the output buffer. Each name fragment subsequent to the first fragment is treated sequentially in one of the three following ways.

(1) A name fragment that terminates in a hyphen is prepended to the contents of the output buffer.

(2) A name fragment that does not end with one of the strings in Table 1 (FIG. 5A), that does not start with one of the strings in Table 2 (FIG. 5B), that does not contain any of the strings in Table 3 (FIG. 5C), and that does not contain the string "mer" followed by a character other than "c", is prepended to the output buffer. The instant name fragment, when prepended, is separated from the rest of the buffer by a space character if the instant name fragment is the overall second fragment to be identified and if the first fragment was one of the strings listed in Table 4 (FIG. 5D); otherwise the instant name fragment is separated from the rest of the buffer by a hyphen. (It is to be understood that Tables 1–4 are not necessarily exhaustive, and may be adapted as necessary.)

(3) In all other cases a name fragment is appended to the output buffer with a space character therebetween.

At this point, the uninversion process is complete and makes available the final contents of the output buffer to serve as the uninverted name (step 2050). Preprocessing is complete.

Once preprocessed, the name is divided into a series of fragments (FIGS. 3A–3B, step 1020). In particular, the name is divided into the smallest number of meaningful fragments of a maximum length. For example, "pentane" is not divided into three fragments "penta", "n", and "e", since the latter two fragments would not be meaningful, but rather is divided into two meaningful fragments "pent" and "ane". In a specific embodiment, a fragment is determined to be meaningful ("recognized") if an exact match for the fragment is found in a dictionary of known text strings ("lexicon") that is maintained by the system.

Figure 6:
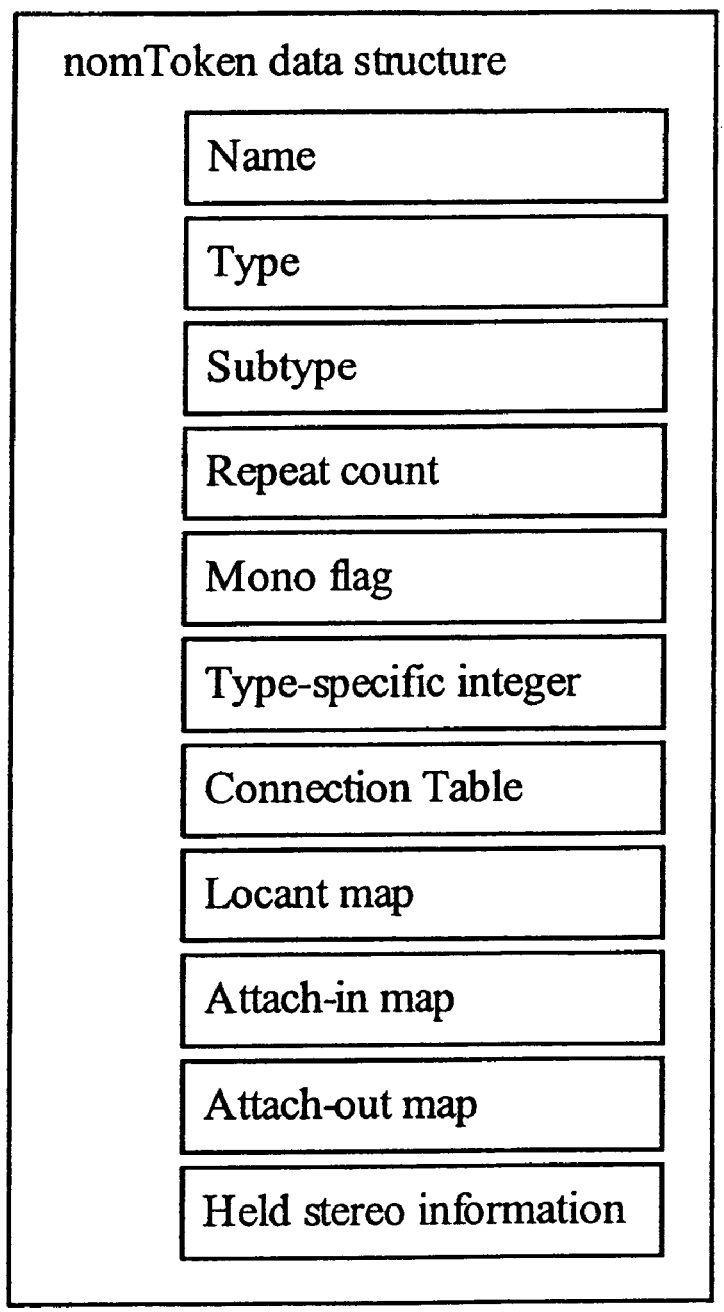

Each known text string is associated in the lexicon with at least one data object known as a nomToken (FIG. 6). A nomToken includes the text of the known text string as its name and is described by Type and Subtype data members, which allow similar fragments to be grouped in accordance with two levels of similarity. Examples of NomTokens are identified in this application's Appendix: NomTokens which is submitted herewith and is incorporated herein, and in which NomTokens are provided in the following format: name{|synonym|synonym| . . . }<space>type<space>subtype<space>data (It is to be understood that the Appendix: NomTokens is not necessarily exhaustive, and may be amended as necessary.)

A text string may be present more than once in the lexicon if the text string is associated with multiple different nomTokens. For example, the text string "amide" is associated with a first nomToken of type kTypeAcid to be used with a name such as "propanamide" and is also associated with a second nomToken, of type kTypeAcidPart2, to be used with a name such as "propanic acid amide". Each nomToken also contains a repeat count and an indicator that indicates whether a repeat count of 1 originated explicitly with the designator "mono", and other optional type-specific information. In a specific embodiment, some of the fields of the nomToken are completed within the lexicon, and others are populated through further processing.

Four data objects within a nomToken record the nomToken's chemical significance: a connection table, a locant map, an attach-in map, and an attach-out map. The connection table includes information that specifies which atoms are connected to which bonds and information regarding characteristics such as atom types, charges, and isotopy. The locant map associates names of individual atoms with respective specific locations in the connection table. For example, an atom named "2" in "2-hydroxy-propanoic acid" may be a specific one of the carbon atoms, and a "3" atom may be a different one of the carbon atoms. Multiple locants can refer to the same atom: "beta" may refer to the same atom as did "2" above.

The attach-in map functions similarly to the locant map and stores a list of atoms identified in the connection table that are considered to be awaiting attachment. Such a list is particularly useful when constructing structures of esters of acids. The attach-out map associates a specific bond order to an attachment. For example, after the phrase "oct-3-ylidene" is interpreted, an entry in the attach-out map indicates that the "3" atom in the "oct" group should have an attachment of order 2. For both the attach-in and attach-out maps, the actual construction of the attachments is performed later in the process.

An attach-in indicates an atom that, in at least some circumstances, preferentially has another fragment attached to it. For example, "acetate" has four atoms: two carbons and two oxygens. A proper interpretation of "methyl acetate" specifies that the methyl group is attached to a particular one of the oxygens. For a portion of the processing period, between the time that "acetate" is handled and the time that "methyl" is attached to it, an attach-in exists on that particular one of the oxygens. Then, when it is time to add the "methyl" fragment, the position indicated by the attach-in is where the "methyl" fragment is attached to the acetate.

In an example involving an attach-out, a fragment "prop" is acquired, indicating a chain of three carbon atoms. There are two ways the fragment can be attached to another fragment: (1) connecting from the first carbon atom, which would cause the three carbons to extend from the other fragment much as a flag extends from a flagpole to flap in the wind, and (2) connecting from the second carbon atom, which produces in a Y-like structure. (Connecting from the third carbon atom is, in most cases, equivalent to connecting from the first carbon atom.) One way that an attach-out may be added to a structure is via the fragment "yl". When interpreting the fragment "propyl", an attach-out is created at the default atom, which is the first carbon atom in this particular case. A name such as "propylbenzene" is consistent with the three carbon atoms of the "propyl" group sticking out in a row from the benzene fragment. On the other hand, the positioning of the attach-out may be specified explicitly. For the fragment "prop-2-yl", the attach-out is attached to the central carbon atom. A name such as "prop-2-ylbenzene" specifies that the three carbon atoms from the "prop" group are attached to the benzene in the Y-like pattern.

A locant is a name for a specific atom. In the "prop-2-ylbenzene" example above, "2" is a name for the second atom in the "prop" three-carbon chain. In this particular case, the name happens to be neatly descriptive since "2" is used for the second atom, but such a situation cannot be assumed. Each atom may have zero locants, one locant, or multiple locants. For example, "prop-beta-yl" would be the same as "prop-2-yl"; the central atom actually has three locants that can be used interchangeably: "2", "b", and "beta". Additionally, the set of locants for a given nomToken may change (i.e., one or more may be added, and one or more may be removed as no longer valid) during the course of processing.

As the preprocessed name is parsed into fragments, a parallel list is derived from the nomTokens corresponding to each fragment (step 1030). If a fragment is represented by more than one nomToken, the nomToken having the highest-ranked type is chosen, at least initially. Punctuation characters including spaces and commas are interpreted as delimiting adjacent fragments, but are not preserved. Unrecognized fragments are converted into nomTokens of type kTypeUnknown and are included in the given order relative to the recognized nomTokens. The parallel list also stores, for each nomToken, an identification of the type of character that immediately preceded the fragment in the preprocessed name: an open parenthesis, bracket, brace, or the start of the name; a space character; or another type of character.

The recognition of parentheses and other enclosing marks, if any, is integral to the name fragmentation process. During the fragmentation, the phrase surrounded by the innermost pair of enclosing marks is parsed as a unit, and is then consolidated as a unit according to a consolidation process described below with respect to the full name. Accordingly, each group within a set of enclosing marks is treated as a single unit, which is consistent with the syntactic meaning of enclosing marks. All levels of enclosing marks are handled in the same way, recursively.

When complete, the list of nomTokens is examined sequentially to determine whether any series of 2 . . . n adjacent nomToken names could be concatenated into a larger "buildable" nomToken (step 1040). This is due at least in part to the fact that a small number of chemical terms are commonly expressed with included punctuation, which the fragmentation process uses to divide the input name. For example, the phrase "mg/ml" could be interpreted as possibly unrecognized nomTokens "mg" and "ml". Accordingly, "mgml" is recognized as a nomToken of type kTypeBuildable, which allows the two nomTokens "mg" and "ml" to be combined into one nomToken. The resulting nomToken of type kTypeBuildable is then converted to a nomToken of identical name and next-highest rank. For example, a fragment "xxxx" may be associated with three nomTokens, all named "xxxx", with respective values of 73, 42, and 21. The fragment may start off with the nomToken of value 73 and then may be converted to the "next-highest rank" nomToken, of value 42, and may subsequently be converted to the next "next-highest rank" nomToken, of value 21.

The list of nomTokens is searched for a nomToken of type kTypeStopword, examples of which are identified in the Appendix: NomTokens (step 1050). If such a nomToken is found, the found nomToken and all subsequent nomTokens are removed from the list and are discarded (step 1060). This is due at least in part to the fact that chemical names are commonly found with additional descriptive text immediately following (e.g., "acetic acid" followed by "99% solution"), where the descriptive text does not contribute any information regarding the chemical structure of the chemical substance. The descriptive text is recognized and removed so that the remainder (e.g., "acetic acid") can be analyzed effectively.

At the conclusion of the framentation process, the text string of the original input name has been successfully divided into one or more substrings, and a list of nomTokens has been constructed corresponding to a list of the substrings. The fragmentation process has focused primarily on information contained in the text itself (e.g., the sequence of characters and punctuation), not on the chemical significance of the resulting nomTokens.

A consolidation process derives, from a list of nomTokens, a smaller list that contains fewer nomTokens, e.g., one nomToken (step 1070). The consolidation process examines the environments of the nomTokens, i.e., the types and subtypes of each nomToken and other nearby nomTokens, and then, in each case, joins two or more nomTokens into a single replacement nomToken, as described below.

The consolidation process may determine that one or more nomTokens are misidentified. For example, a nomToken of type kTypeNatDeriver serves only to modify another nomToken that refers to a natural product, i.e., a nomToken of type kTypeRoot and subtype kSubtypeNatural. NomTokens of kTypeRoot pertain to collections of atoms connected by collections of bonds in a predetermined pattern, and correspond roughly to "root" or "core" fragments of a molecule.

In the absence of a nomToken that refers to a natural product, the nomToken of type kTypeNatDeriver is determined to have been misidentified. In such a case, the nomToken of type kTypeNatDeriver is converted to an identically-named nomToken of next-highest-rank, if any. If no identically-named nomToken of lower rank is found, the nomToken is converted to a nomToken of type kTypeUnknown, which is the lowest possible rank.

One suitable system of ranking of types is described herein (see also Appendix: NomTokens and the source code appendix under "enum nomTokenType"), but there are other suitable systems of ranking as well. With any suitable system of ranking, all consolidation steps are to be considered in light of the characteristics of that system of ranking. In at least some cases, it is important that nomTokens be considered and acted upon in a particular order, so that nomTokens of the necessary rank are available when needed, and have not already been examined and converted to other nomTokens of lower rank.

The consolidation process begins with environments that are most specific. For example, characteristically, nomTokens of type kTypeCrown are immediately preceded and immediately followed by numerals, which are represented by nomTokens of type kTypeUnknown, for fragments consisting entirely of numeric digits. If such environments are found, a connection table for a crown ether may be constructed, and all three nomTokens may be replaced by a single nomToken containing the connection table. A nomToken of type kTypeCrown that is not preceded and followed by numerals is determined to be misidentified and is, as described above, therefore converted into the next-highest-ranked nomToken and retained in the list for later processing.

Consolidation continues with a series of less-localized nomenclature types characterized as sometimes appearing in multiple non-adjacent fragments. For example, interpretation of atomic chains may be performed at this stage. A nomToken of type kTypePrefix, such as "pent" or "penta", may refer implicitly to an alkyl or heteroatomic chain. The "penta" in "pentadiene" necessarily refers to a five-carbon chain. In a suitable environment, when followed by a nomToken of kTypeYl, such as "yl", "penta" is identified as referring to an alkyl chain, an appropriate connection table is constructed, and the nomToken is converted to kTypeRoot, which is described above. In a different environment, when followed by a nomToken of kTypeRoot, "penta" indicates that the root structure should be repeated, and its original designation as kTypePrefix is retained for later handling.

The following description is with respect to the example of "penta". A pentane structure is a string of 5 carbon atoms separated by single bonds, with a sufficient number of hydrogen atoms to make 4 attachments on each carbon: CH3—CH2—CH2—CH2—CH3. This is an example of an atomic chain. Pentasilane is a similar structure with silicon atoms instead of carbon atoms: SiH3—SiH2—SiH2—SiH2—SiH3. This is an example of a heteroatomic chain. "Silane" is the single molecule SiH4, where the central atom is connected to each of the four surrounding atoms by a single bond. However, "pentasilane" is not properly interpreted to mean arranging 5 individual silane molecules next to each other to produce SiH4 SiH4 SiH4 SiH4 SiH4. On the other hand, "hydroxide" refers to a single molecule OH—, where the negatively-charged oxygen is connected to the hydrogen by a single bond, and "pentahydroxide" is in fact properly interpreted to mean arranging 5 individual hydroxide molecules next to each other to produce OH— OH— OH— OH— OH—.

Cyclic systems are created and aromatic rings are fused at this point in the processing. As shown, the order of interpretation is important in the individual sections as well as in the interpretation process as a whole. A name such as "benzocyclooctene" implies that chains (kTypePrefix, treated as described above) are to be interpreted first and then are to be closed (kTypeCyclo) before being submitted for participation in ring fusions (kTypeBenzo).

At this point, portions have been identified within the greater set of name fragments that correspond to structures known as "root" or "core" structures.

After the main root portions of the name are identified, the consolidation process continues with nomTokens that directly modify the main root portions. Such directly modifying nomTokens generally correspond to grammatical prefixes and suffixes within the original input name. In at least one embodiment, many nomTokens representing traditional chemical functional groups are recognized at this stage, including acids in variations, radical suffixes such as "-yl," and prefixes of heterocyclic "aza" nomenclature. Since there are many text strings that correspond to multiple nomTokens for functional groups, it is advantageous to examine the environments carefully for details.

In the last stages of the consolidation process, multiple large groups are joined, so that typically, for example, ligands are joined to root structures, cations to anions, and esters to acids.

An attach-out map having at least one remaining entry is present at the end of the consolidation process for a name such as "methyl" that is usually intended to be joined to another name fragment. An appropriate radical is added to the connection table for such remaining entry in the attach-out map, wherein, for example, "methyl" is a monoradical and "methylidene" is a diradical.

The consolidated list of nomTokens is examined for any remaining nomTokens of type kTypeUnknown having names that correspond to known stereochemical indicators (step 1080). Stereochemistry is considered at this point because stereochemistry may be determined by the entire contents of a connection table. If a suitable nomToken is found, the appropriate stereochemistry is added to the connection table, and the nomToken representing the stereochemical indicator is removed (step 1090).

As shown, each action following the fragmentation of the original input name has attempted to reduce the number of nomTokens in the resulting list. If the list has been reduced by this point to a single nomToken, the nomToken's connection table, if present, represents the structure corresponding to the original input name. In such a case, a representation of the structure (e.g., an image of the structure) is derived from the connection table and is presented to the user (step 1100). (See, e.g., the above-cited simultaneously filed application.) If more than one nomToken is present, or if the single nomToken lacks a connection table, it is determined that the original input name in uninterpretable and an appropriate error message is presented instead (step 1110).

An example using a specific chemical name is now described. A name "Phenacyl bromide, p-napthoxy" is submitted for processing. The name is preprocessed, including being converted to all lowercase characters, resulting in "phenacyl bromide, p-napthoxy". A common typographical error "napth" is converted to "naphth", which produces "phenacyl bromide, p-naphthoxy". The name is uninverted, leaving "p-naphthoxy-phenacyl bromide".

Figure 7C:
Figure 7C:

The name is divided into six recognized fragments and a list of six corresponding nomTokens is created. These six nomTokens, with their types, subtypes, previous characters, and a graphical depiction of their connection tables, are shown in FIG. 7A.

The list of nomTokens is examined for recognized environments. The first recognized environment is found when the list is examined for amino acids. No amino acids are found in the list, but one nomToken ("yl") of type kTypeEnderAminoAcid is present. Such a nomToken, being meaningful only in the context of amino acids, is not meaningful in this list that contains no amino acids. Accordingly, the nomToken of type kTypeEnderAminoAcid is converted to the next-highest-ranked nomToken of identical name, which in this case is of type kTypeSuffix and subtype kSubtypeYl (see FIG. 7B).

The next recognized environment is found in preparing to create ortho/peri fused ring systems. One example of such an environment requires, among other things, adjacent tokens of types kTypeOPFuser and kTypeRoot. In this list of nomTokens, a nomToken of type kTypeOPFuser exists but is followed by a nomToken of type kTypeInfix instead. Therefore, the nomToken of type kTypeOPFuser is determined not to be meaningful in this context, and is converted to the next-highest-ranked nomToken of the same name, which in this case is of type kTypeRoot and subtype kSubtypeUnknown (see FIG. 7C).

The list is examined for nomTokens of type kTypeSuffix. Such a nomToken ("yl") is found, and is found to be preceded by a nomToken of type kTypeRoot, which results in a recognized environment. With respect to this recognized environment, an entry is added to the attach-out map of the root structure. In the absence of an explicit locant, the attach-out is assigned to the first atom in the connection table that has sufficient valences, which in this case is the terminal carbon (see FIG. 7D in which the attach-out is represented by a black diamond). The nomToken of kTypeSuffix is removed from the list, leaving five nomTokens in the list.

One of the nomTokens remaining in the list ("bromide") had been preceded by a space character in the preprocessed name. The space character may be chemically significant and is processed at this point. The list is divided into two smaller sublists, one of which contains the four nomTokens before the "bromide" nomToken, and the other of which contains the "bromide" nomToken only.

The first of the sublists is examined for nomTokens of type kTypeInfix. In this case, one nomToken of this type, "oxy", is found, and is preceded by another nomToken of type kTypeRoot, which results in a recognized environment. In this environment, the entire contents of the connection table of the kTypeInfix nomToken are merged into the connection table of the root. Additionally, a bond is created between the first atoms with sufficient free valences originating in the two connection tables. Any entries (one in this case) in the attach-in and attach-out maps of the nomToken of type kTypeInfix are copied to corresponding atoms in the merged connection table. The subtype of the root structure is changed to kSubtypeInfix. The nomToken of type kTypeInfix is then discarded. The second of the sublists is similarly examined, but no changes are necessary in this case. At this point, the entire list has four nomTokens (see FIG. 7E).

Figure 7F:
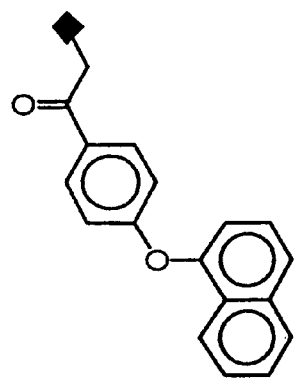

In this example, only one other environment is recognized in the sublists, and is found in the first sublist. The first sublist contains a nomToken of kTypeRoot ("phenacyl") that is preceded by another nomToken of kTypeRoot ("naphthoxy") that has exactly one entry in its attach-out list. Furthermore, the further preceding nomToken is of type kTypeUnknown and has a name ("p") that corresponds exactly to one of the entries in the locant map of "phenacyl". Therefore, the connection tables for "naphthoxy" and for "phenacyl" are combined, and a bond is indicated between the atom referenced in the attach-out map of "naphthoxy" and the atom referenced by the "p" entry in the locant map for "phenacyl". Accordingly, with respect to the three nomTokens involved, two are discarded and the resulting connection table is stored in the third, which leaves two nomTokens in the entire list (FIG. 7F), with exactly one nomToken in each sublist. As no other environments are recognized in either sublist, the two sublists are recombined.

Figure 7G:
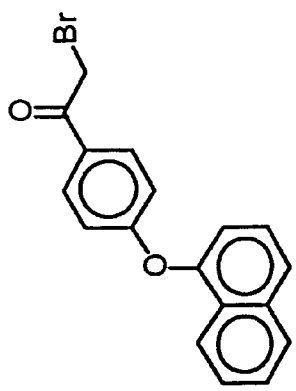

The last environment that is recognized consists of a nomToken of type kTypeCounterion following a nomToken of type kTypeRoot, each of which nomToken has at least one entry in its respective attach-out list. In this environment, the two connection tables are merged, and a bond is indicated between the two atoms referenced by the attach-out lists (FIG. 7G).

At this point, the list has a single nomToken, which is of type kTypeRoot and has a non-empty connection table. As the attach-out list has no entries, no radicals need to be added to the connection table. The name has been fully parsed. The structure shown in FIG. 7G is the correct structure for the original name "phenacyl bromide, p-napthoxy", and is presented to the user.

All or a portion of the procedures described above may be implemented in hardware or software, or a combination of both. In at least some cases, it is advantageous if the technique is implemented in computer programs executing on one or more programmable computers, such as a personal computer running or able to run an operating system such as UNIX, Linux, Microsoft Windows 95, 98, 2000, or NT, or MacOS, that each include a processor, a storage medium readable by the processor (including volatile and non-volatile memory and/or storage elements), at least one input device such as a keyboard, and at least one output device. Program code is applied to data entered using the input device to perform the technique described above and to generate output information. The output information is applied to one or more output devices such as a display screen of the computer.

In at least some cases, it is advantageous if each program is implemented in a high level procedural or object-oriented programming language such as Perl, C, C++, or Java to communicate with a computer system. However, the programs can be implemented in assembly or machine language, if desired. In any case, the language may be a compiled or interpreted language.

In at least some cases, it is advantageous if each such computer program is stored on a storage medium or device, such as ROM or optical or magnetic disc, that is readable by a general or special purpose programmable computer for configuring and operating the computer when the storage medium or device is read by the computer to perform the procedures described in this document. The system may also be considered to be implemented as a computer-readable storage medium, configured with a computer program, where the storage medium so configured causes a computer to operate in a specific and predefined manner.

Other embodiments are within the scope of the following claims. For example, the system may be combined with one or more external databases of names and structures, so that a chemical name present in the external databases but not otherwise parsable would still produce a structure. In another example, non-English chemical names could be interpreted as well or instead. In another example, the fragmentation of the initial chemical name may be varied, e.g., by using different or extended lists of known chemical name fragments.

What is claimed is:

1. A method for use in deriving chemical structural information, comprising the steps of:
   acquiring a chemical name;
   preprocessing the name to standardize its formatting;
   dividing the name into a series of meaningful text string fragments;
   associating each meaningful text string fragment with at least one data object known as a nomToken, thereby creating a list of one or more nomTokens, wherein each text string fragment comprises the name of the corresponding nomToken, and wherein each nomToken comprises:
      a connection table,
      a locant map that associates names of individual atoms with respective specific locations in the connection table,
      an attach-in map that stores a list of atoms identified in the connection table that are considered to be awaiting attachment, and
      an attach-out map that associates a specific bond order to an attachment;
   and wherein each nomToken is classified by Type and Subtype from a ranked list of Types and Subtypes;
   consolidating two or more nomTokens into a single replacement nomToken; and
   repeating the consolidating step until only one nomToken remains, wherein the connection table of the remaining nomToken corresponds to the structure of the chemical name.

2. The method of claim 1, further comprising the steps of:
   deriving a graphical representation of the structure of the chemical name from the connection table of the single remaining nomToken; and
   presenting the graphical representation of the structure to the user in the form of output.

3. The method of claim 1, wherein the consolidating step further comprises the steps of:
   examining the Types and Subtypes of the nomTokens for the first Type from a predetermined list of Types; and
   determining if the Type and Subtype of the nomToken of the first Type from the predetermined list of Types is compatible with one or more Type and Subtype of the remaining nomTokens; and
   joining a group of one or more nomTokens of the remaining nomTokens with the nomToken of the first Type into a single replacement nomToken, wherein the connection table, locant map, attach-in map, and attach-out map of each nomToken in the group and of the nomToken of the first type are used to create an appropriate connection table for the replacement nomToken when the Types and Subtypes of the nomTokens in the group are compatible with the Type and Subtype of the nomToken of the first Type.

4. The method of claim 1, wherein the consolidating step further comprises the step of:
   identifying one or more text string fragments that represent the root portion of the chemical name;
   examining the remaining fragments of the text string fragment for fragments that directly modify the root portion of the chemical name.

5. The method of claim 1, wherein the preprocessing step comprises one or more of the following steps:
   converting the name to all lower-case characters;
   identifying and correcting typographical errors;
   spelling out uncommon characters of chemical significance; and
   determining if the chemical name is inverted and converting the chemical name to a corresponding uninverted form.

6. The method of claim 1, wherein the number of meaningful text string fragments is the smallest number of meaningful fragments of a maximum length.

7. A method for use in deriving chemical structural information, comprising the steps of:
   a) acquiring a chemical name;
   b) preprocessing the name to standardize formatting;
   c) dividing the name into a series of meaningful text string fragments;
   d) associating each meaningful text string fragment with at least one data object known as a nomToken, wherein each text string fragment comprises the name of the nomToken, and wherein
      each nomToken comprises:
         a connection table,
         a locant map that associates names of individual atoms with respective specific locations in the connection table,
         an attach-in map that stores a list of atoms identified in the connection table that are considered to be awaiting attachment, and
         an attach-out map that associates a specific bond order to an attachment; and wherein
      each nomToken is initially identified with the highest Type and Subtype from a ranked list of Types and Subtypes whose name matches the name of the text string fragment;
   e) examining the Types and Subtypes of the nomTokens for the first Type from a predetermined list of Types;
      examining the remaining nomTokens for compatible Types and Subtypes when a nomToken of the first Type is identified;
   f) for each set of compatible nomTokens, modifying the associated nomTokens, wherein the modifying step comprises:
      i) combining two or more nomTokens into a single replacement nomToken;
      ii) converting one or more nomTokens to the next highest ranked nomTokens of identical name;
   g) repeating steps e) and f) until all Types have been examined, wherein for each repeating step, the nomTokens are examined for the next Type from the predetermined list of Types; and wherein
   h) when only one nomToken remains, the connection table of the remaining nomToken corresponds to the structure of the chemical name.

8. The method of claim 7, wherein one or more nomTokens is converted to the next highest ranked nomToken when a set of compatible nomTokens is not identified.

9. The method of claim 7, wherein the number of meaningful text string fragments is the smallest number of meaningful fragments of a maximum length.

10. Computer software, residing on a computer-readable storage medium, comprising a set of instructions for use in a computer system to derive chemical structural information, the instructions causing the system to:
acquire a chemical name;
preprocess the name to standardize its formatting;
divide the name into a series of meaningful text string fragments;
associate each meaningful text string fragment with at least one data object known as a nomToken thereby creating a list of nomTokens, wherein each text string fragment comprises the name of the corresponding nomToken, and wherein each nomToken comprises:
a connection table,
a locant map that associates names of individual atoms with respective specific locations in the connection table,
an attach-in map that stores a list of atoms identified in the connection table that are considered to be awaiting attachment, and
an attach-out map that associates a specific bond order to an attachment;
and wherein each nomToken is classified by Type and Subtype from a ranked list of Types and Subtypes;
consolidate two or more nomTokens into a single replacement nomToken; and
repeat the consolidating step until only one nomToken remains, wherein the connection table of the remaining nomToken corresponds to the structure of the chemical name.

11. The computer software of claim 10, further comprising instructions for use in a computer system to:
derive a graphical representation of the structure of the chemical name from the connection table; and
present the graphical representation of the structure to the user in the form of output.

12. The computer software of claim 10, wherein the consolidating step further comprises instructions for use in a computer system to:
examine the Types and Subtypes of the nomTokens for the first Type from a predetermined list of Types;
determine if the Type and Subtype of the nomToken of the first Type from the predetermined list of Types is compatible with one or more Type and Subtype of the remaining nomTokens; and
join a group of one or more nomTokens of the remaining nomTokens with the nomToken of the first Type into a single replacement nomToken, wherein the connection table, locant map, attach-in map, and attach-out map of each nomToken in the group and of the nomToken of the first type are used to create an appropriate connection table for the replacement nomToken when the Types and Subtypes of the nomTokens in the group are compatible with the Type and Subtype of the nomToken of the first Type.

13. The computer software of claim 10, wherein the consolidating step further comprises instructions for use in a computer system to:
identify one or more text string fragments that represent the root portion of the chemical name; and
examine the remaining fragments for those that directly modify the root portion of the chemical name.

14. The computer software of claim 10, wherein the preprocessing instructions further comprises one or more of the following instructions for causing the system to:
convert the name to all lower-case characters;
identify and correct typographical errors;
spell out uncommon characters of chemical significance; and
determine if the chemical name is inverted and converting the chemical name to its uninverted form.

15. The computer software of claim 10, wherein the number of meaningful text string fragments is the smallest number of meaningful fragments of a maximum length.

16. Computer software, residing on a computer-readable storage medium, comprising a set of instructions for use in a computer system to derive chemical structural information, the instructions causing the system to:
a) acquire a chemical name;
b) preprocess the name to standardize formatting;
c) divide the name into a series of meaningful text string fragments;
d) associate each meaningful text string fragment with at least one data object known as a nomToken, wherein each text string fragment comprises the name of the nomToken, and wherein
each nomToken comprises:
a connection table,
a locant map that associates names of individual atoms with respective specific locations in the connection table,
an attach-in map that stores a list of atoms identified in the connection table that are considered to be awaiting attachment, and
an attach-out map that associates a specific bond order to an attachment; and wherein
each nomToken is initially identified with the highest Type and Subtype from a ranked list of Types and Subtypes whose name matches the name of the text string fragment;
e) examine the Types and Subtypes of the nomTokens for the first Type from a predetermined list of Types;
examine the remaining nomTokens for compatible Types and Subtypes when a nomToken of the first Type is identified;
f) for each set of compatible nomTokens, modify the associated nomTokens, wherein the modifying step comprises instructions that causes the system to:
i) combine two or more nomTokens into a single replacement nomToken;
ii) convert one or more nomTokens to the next highest ranked nomToken of identical name;
g) repeat steps e) and f) until all Types have been examined, wherein for each successive repeating step, the nomTokens are examined for the next Type from the predetermined list of Types; and wherein
h) when only one nomToken remains, the connection table of the remaining nomToken corresponds to the structure of the chemical name.

17. The computer software of claim 16, wherein one or more nomTokens is converted to the next highest ranked nomToken when a set of compatible nomTokens is not identified.

18. The computer software of claim 16, wherein the number of meaningful text string fragments is the smallest number of meaningful fragments of a maximum length.

* * * * *